United States Patent [19]

Kapadia et al.

[11] Patent Number: 4,816,028
[45] Date of Patent: Mar. 28, 1989

[54] WOVEN VASCULAR GRAFT

[76] Inventors: Indu Kapadia, 33 Front St., Denville, N.J. 07834; Ibrahim M. Ibrahim, 130B Knickerbocker Rd., Closter, N.J. 07624

[21] Appl. No.: 68,662

[22] Filed: Jul. 1, 1987

[51] Int. Cl.⁴ .............................................. A61F 2/06
[52] U.S. Cl. ...................................... 623/1; 623/12; 623/66; 128/334 R; 139/387 R; 428/257; 428/36.1
[58] Field of Search ............... 128/334 R; 139/387 R, 139/388, 419; 428/36, 257, 258; 623/1, 12, 13, 66

[56] References Cited

U.S. PATENT DOCUMENTS

| | | | |
|---|---|---|---|
| 955,541 | 4/1910 | Peterson | 139/387 R |
| 1,139,467 | 5/1915 | Cole | 139/388 |
| 3,878,565 | 4/1975 | Sauvage | 623/1 |
| 4,047,252 | 9/1977 | Liebig et al. | 623/1 |
| 4,282,011 | 8/1981 | Terpay | 428/258 |
| 4,517,687 | 5/1985 | Liebig et al. | 623/1 |
| 4,530,113 | 7/1985 | Matterson | 623/1 |

FOREIGN PATENT DOCUMENTS

| | | | |
|---|---|---|---|
| 0015421 | of 1885 | United Kingdom | 139/419 |
| 0825183 | 12/1959 | United Kingdom | 623/12 |

Primary Examiner—Richard J. Apley
Assistant Examiner—Paul Prebilic
Attorney, Agent, or Firm—Rosen, Dainow & Jacobs

[57] ABSTRACT

A woven tubular vascular prosthesis having alternating plain/twill weave and two pairs of double leno weave of texturized synthetic fiber of 64 denier/144 filament has sufficiently low porosity that preclotting is unnecessary to avoid hemorrhaging and unravelling is prevented even where the graft is cut at an oblique angle.

20 Claims, 3 Drawing Sheets

WOVEN VASCULAR GRAFT

BACKGROUND OF THE INVENTION

This invention is in the field of vascular grafts made of synthetic fibers that are used in a variety of vascular surgical procedures. Particular interest herein is to grafts used to replace occluded portions of arteriosclerotic vessels or used to form new blood pathways in vascular reconstruction procedures, as generally disclosed in U.S. Pat. Nos. 4,517,687, 4,047,252, 4,530,113, and 3,878,565.

There are basically three kinds of grafts on the market, namely extruded, knitted and woven. Extruded or non-woven grafts are generally strong and non-porous which precludes subsequent hemorrhaging, but have numerous undesirable characteristics. The total lack of porosity prevents subsequent tissue ingrowth which has been considered highly desirable. Also these grafts are relatively stiff and nonconforming and thus difficult to handle and implant.

Knitted grafts have numerous advantages over the extruded ones, namely high porosity, flexibility, softness and a velour type surface. Accordingly, they conform easily which reduces surgeon's and patient's time in the operating room, and the porosity and velour surface allow considerable endothelialization (tissue ingrowth). The principal disadvantage of knitted grafts is that the porosity is so great, hemorrhaging will occur unless the graft is preclotted, this being a separate step requiring about fifteen minutes for immersion of the graft in a quantity of about 100-150 cc of blood of the patient, after which the graft is allowed to stand for clotting to occur. Preclotting substantially prevents hemorrhaging, while tissue ingrowth can still proceed; however sometimes preclotting is not permissible as where the patient has been anti-coagulated or has bleeding diathesis. In these cases a knit graft cannot be used. Final negative considerations about knitted grafts are the recent belief that the high velour interior surface inherent in knit fabric may simply act to collect dead tissue and disrupt blood flow, that tissue ingrowth into the high velour exterior surface may be less significant than previously predicted, and that knitted grafts expand and stretch more than other types.

Woven grafts have certain advantages over both extruded and knitted grafts in that porosity is lower, so that preclotting is not required and the surface are more uniform for smoother blood flow. A disadvantage of woven grafts is that they are relatively stiffer and less conforming than knit grafts and thus more difficult and time consuming for the surgeon to use.

A prospective and not currently available graft is a knitted tube coated in manufacture with a substance such as collagen to prevent initial bleeding following implantation. This collagen coating obviates the necessity for typical preclotting during surgery; however, such coating renders the tube stiffer and more difficult to handle during implantation. Also such a coated product is considerably more expensive than a simple woven graft.

The above description of prior art grafts shows some of the numerous parameters considered in the selection of vascular grafts. Additional factors include tissue compatibility, nonthrombogenicity of the surface, deterioration of the graft with time, resistance to infection, and resistance to kinking at the joints of the patient.

Typically in the manufacture of both knitted and woven grafts the tubular body is crimped to form circumferential corrugations or ribs that provide strength and resilience against kinking and collapsing of the tube and narrowing of the lumen from bending or twisting. Known woven grafts use a polyester such as Dacron ® (polyethylene terephythalate) yarn, Type 56 made by Dupont for approximately 30 years and designated 40 denier/27 or 70 denier/34, the 40d/27 representing 40 grams of weight per 9000 meters of yarn which yarn comprises 27 filaments, or 1.48 denier per filament. Dacron ® is a registered trademark for E. I. Dupont for polyester yarn. The selection of 40d/27 yarn in single or double ply as the standard of the industry has been dictated by what was available on the market and what has been approved by the F.D.A. Prior patents referred to above describe more fully this standard yarn, which is also texturized in a standard way, i.e. twisting the fibers at about 50,000 rpm, under 8-15 grams of tension at about 450° F.

The weaving of arterial grafts is done on known weaving apparatus with a matrix of weft or fill threads into which are woven a pattern of warp threads, some of which are twill or velour weave to later produce the velour loops on the inner and/or outer surfaces. As is known, these twill threads for the velour loops are preshrunk, so that upon the shrinking of the completed graft tube made of otherwise unshrunk yarn, all threads will shrink except the velour ones which will extend outward from the surface as loops to subsequently receive the tissue ingrowth.

In view of the above-described function parameters and the differences between the various prior art grafts, compromises in characteristics are required with each selection. More specifically, if one wishes softness and pliability and porosity, the choice must be a knit graft with the required preclotting.

SUMMARY OF THE INVENTION

The new vascular graft of this invention provides a combination of critical advantages that have been previously available only partially with knit grafts and partially with woven grafts. More particularly the new graft has the low porosity of woven grafts, the softness and pliability of knits, and the non-fraying feature of extruded grafts. This has become possible by the selection of a high denier, high filament or lower denier, higher filament (75d/72 and 64d/144) polyester yarn which is texturized under new conditions, and woven in a new weave pattern. The weave is designed as a double leno-twill weave with repeating sets of double-lenos, with a flat interior surface and a velour outer surface to aid in healing via endothelization. The weave includes repeating sets of double leno and plain/twill threads, where a leno is one pair of warp threads twisted or crossed one over the other between fill threads, or double leno or double leno set is a pair of adjacent lenos, and each plain/twill set comprises at least four warp threads alternating as plain, twill, plain, twill. What is meant by a twill weave is a fabric woven typically as 3/1, i.e. at least over three fill threads following under one fill thread. The sets of double lenos are alternated with the plain and twill threads to lock the weft threads, and thus substantially prevent fraying or unravelling of the fill threads when the end of the tube is cut at an oblique angle. These new woven grafts have lower porosity than knitted grafts, yet have the softness and pliability of knits and still do not require preclotting.

They are thus easier to handle and implant and conform.

DESCRIPTION OF THE PREFERRED EMBODIMENT

Figure 1:
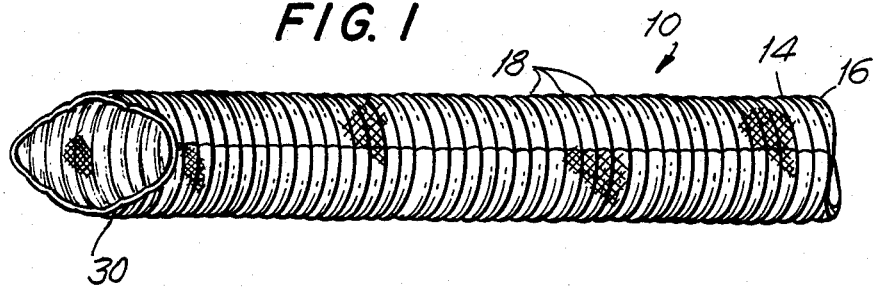
FIG. 1 is a perspective view of a section of woven vascular tube spirally crimped in accordance with this invention.
Figure 2:
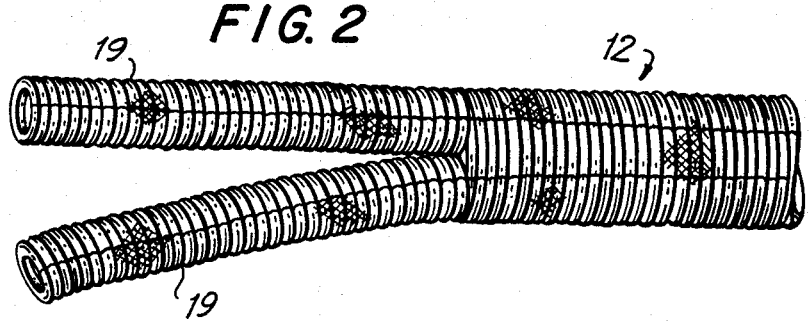
FIG. 2 is a perspective view of a section of woven vascular bifurcated graft spirally crimped in accordance with this invention.

A vascular graft of the present invention is shown as a segment 10 of a straight tube in FIG. 1 and as a bifurcated segment 12 in FIG. 2. Each segment has circumferential ribs 14 defining therebetween grooves 16. The tube is woven from polyester yarns into the tubular shapes shown, with the tubular wall being a weave pattern as represented by the enlarged views in FIGS. 3 and 4. The black lines 18 and 19 in FIGS. 1 and 2 respectively are readily visible to aid the surgeon to avoid twisting the tube during implantation. Optionally, such a line can also be radiopague to indicate more clearly in an X-ray picture the location and condition of the implanted graft. The circular ribs, which may also be helical, add structural stability to the tube for maintaining the lumen open and reduce kinking despite curves along the axis of the graft and subsequent movement or bending of the graft after implantation.

Figure 3:
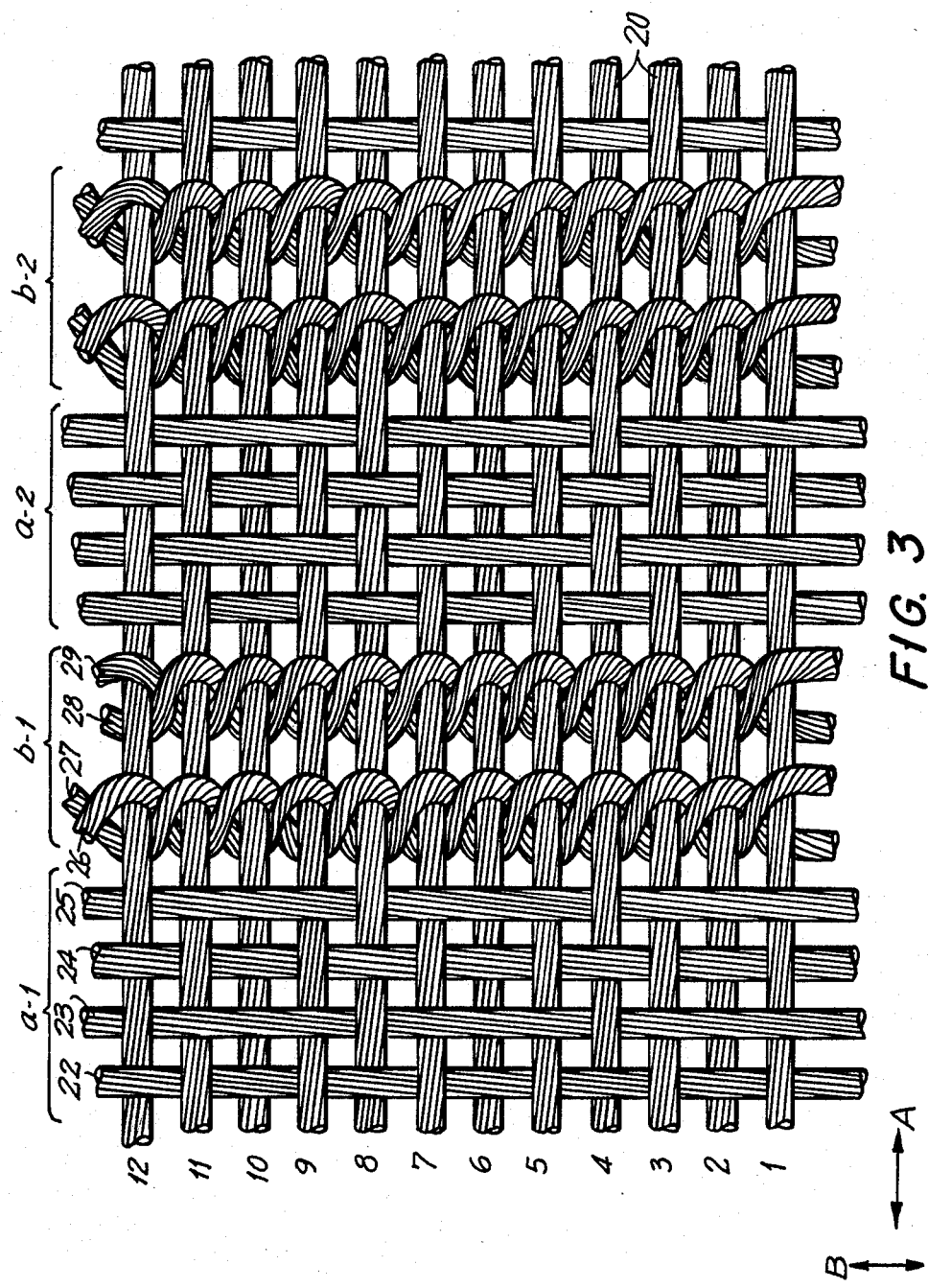
FIG. 3 is a fragmentary plan view of a graft wall surface showing a twill-double leno and gauze weave which has been used in FIG. 1 and FIG. 2.
Figure 4:
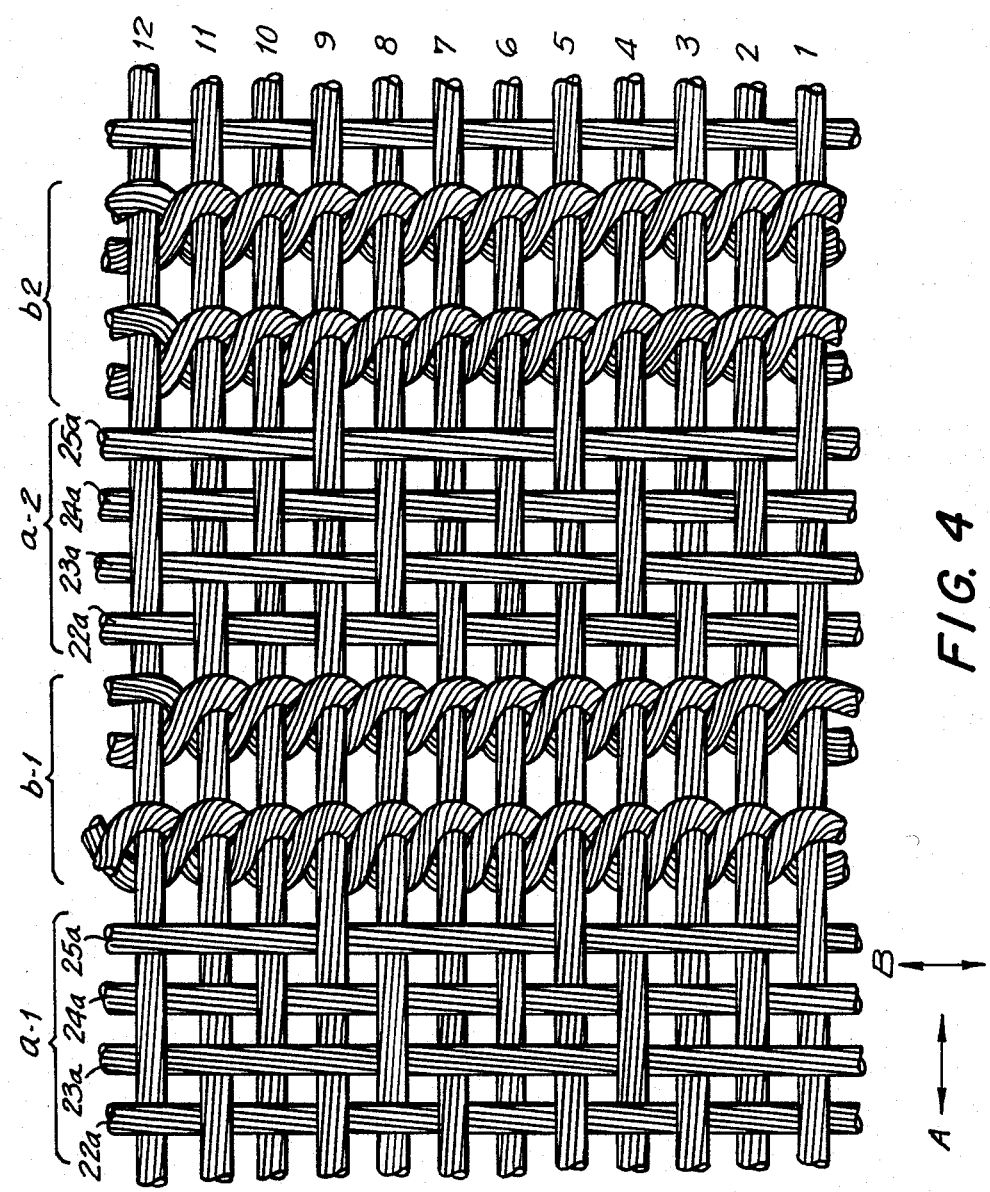
FIG. 4 is a view similar to FIG. 3 showing the alternative method of the twill and double leno and gauze weave pattern.

The fabric of FIGS. 3 and 4 is woven by techniques and apparatus known in industry. The novelty herein concerns the new weave pattern of a yarn that is also new by virtue of its yarn selection and texturizing technique. This yarn and weave combination provide a tubular fabric with highly advantageous characteristics when used as an arterial graft.

The next following section will describe the new weave pattern; the yarn itself and the texturizing will be described in later sections. To create the tubular grafts of this invention weaving apparatus known in the art is used. As represented in FIG. 3, weft or fill threads 1-12 in the direction of the arrow A are set up at about 60 to 80 picks per inch and preferably at about 72 picks per inch, and warp threads are woven in the direction of the arrow B transverse or perpendicular to direction A at about 140-170 per inch. After shrinkage the weave comprises warp threads in the range of 140 to 170 threads per inch and weft threads in the range of 70 to 80 threads per inch. In the enlarged FIGS. 3 and 4 the threads appear widely spaced apart; however, in actuality the threads are tightly packed forming a fabric of the graft wall that is substantially nonporous to hemorrhaging or blood leakage.

The weave pattern of FIG. 3 comprises regular fill threads 20 and repeat sets of warp threads comprising from left to right, set a-1 of alternating plain gauze and twill threads, set b-1 of two pairs of twisted threads forming one double-leno set a-2 the repeat of a-1, and set b-2 the repeat of b-1. In set a-1 threads 22 and 24 are plain 1/1 gauze weave, i.e. over one fill thread, under the next, over the next, etc. Threads 23 and 25 are 3/1 twill weave, in that each goes under one fill thread, over the next three fill threads, under the next one fill thread, etc. More specifically, warp thread 22 goes under fill thread 1, over fill 2, under fill 3, over 4, etc., and warp (twill) thread 23 goes over fill threads 1, 2 and 3, under 4, over 5, 6 and 7, under 8, etc. Threads 23 and 25 are pre-shrunk, so that later when the tube is completed and shrunk, all the threads shrink up to tightly compact the fabric, except the pre-shrunk segments of warp threads that lie "over three fill threads" do not shrink with the fabric but stand out from the top surface of the fabric as velour loops to later better accommodate tissue ingrowth.

The pairs of leno threads 26, 27 and 28, 29 in set b-1 are woven over-under-over-under the fill threads and criss-crossed, one over the other. As represented, these sets b-1 and b-2 of warp threads extending axially in the tube repeat alternately completely around; threads numbered 1, 2, 3, etc. are weft or fill threads extending perpendicular to the warp threads the tube.

Figure 5:
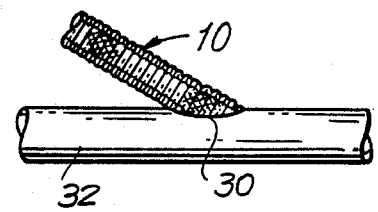
FIG. 5 is a fragmentary elevation view of the graft of Fig. 1 sutured to an artery.

In a typical implantation the end of a tubular graft is cut at an oblique angle to produce a generally oval edge 30 as generally indicated in FIG. 1, which edge is later sutured onto an existing artery 32 as indicated in FIG. 5. An oval edge is preferred to a circular edge from a cut normal to the tube axis, because the resulting oval edge fits the existing artery better and provides a greater length of edge to be sutured and thus a more secure and reliable junction.

Because the cut edge 30 is highly angular relative to the fill or weft threads that are perpendicular to the tube axis and the warp threads, fraying or unravelling of fill threads at the cut edge results. Such unravelling is extremely unsatisfactory because this is the precise area of junction where the graft is sutured to the existing artery and where strength and consistency of the fabric is needed. The sets of double-leno by their criss-cross and twist, lock in the fill threads so that unravelling is prevented or at least minimized.

The repeated and alternating sets of plain/twill and double-leno provide a fabric matrix that has: (a) a generally flat inner surface, (b) velour loops at an appropriate frequency and distribution on the outer surface, and (c) locking double-lenos at sufficient frequency to greatly inhibit unravelling.

FIG. 4 is similar to FIG. 3, but differs in that warp threads 23a which corresponds generally to thread 23 in FIG. 3, is woven such that each "over three picks" loop is displaced axially by one weft thread from the corresponding loop of thread 25a. Accordingly, thread 23a lies under fill thread 4, over fill threads 5, 6 and 7, then under 8; whereas, the next warp thread 25a lies under fill 5, over fills 6, 7 and 8, and under 9. In fabrics where this axial displacement continues with each subsequent twill thread, a diagonal pattern appears in the fabric called a twill. In FIG. 3 where the warp threads 23 and 25 are not relatively displaced axially, the designation is parallel twill. The remaining plain and double-leno threads in FIG. 4 are the same as in FIG. 3.

Whether the warp thread pattern of FIG. 3 or FIG. 4 is used in making a woven graft, the inner surface will be generally flat, the outer surface will include velour loops, and the cut edge will have a greatly reduced likelihood of unravelling. It is also acceptable to vary the number of warp threads i.e. the alternating plain and twill threads, in each set a-1, a-2, etc. in FIGS. 3 and 4 to comprise five, six, seven or more, so long as each set b-1, b-2, etc. comprises at least two pairs of crossed warp threads as shown.

The yarn used in this new fabric graft is preferably polyester (polyethylene terephthalate) of 64 denier/144 filaments available from Tejin Company of Japan. Yarn of this material is biocompatible and long lasting within the body of a patient. Because this yarn has more and thinner filaments than the traditional 40d/27 Dacron yarn (Type 56 of Dupont), each thread has greater vulnerability to breakage, so that new and special texturizing techniques were developed as follows. The new texturizing parameters include: lower spindle speed of 80,000–90,000 rpm compared to the standard 250,000 rpm, lower tension of 4 to 5 grams compared to the standard 8–15 gms, lower heat of 360° F. compared to the standard 450° F. and greater twists per inch of 11/2 compared to ½ turns in prior art. The new texturized yarn is adequately strong and reliable to be appropriate for these arterial grafts. The twill or velour threads are pre-shrunk by known methods. The term "texturized yarn" as used herein regarding the new invention means yarn prepared by the new texturizing parameters described above.

The woven fabric of the graft may be designated 2/64/144 texturized (2 ply 64 denier 144 filaments) or 1/64/144 texturized (1 ply 64 denier 144 filaments), fabricated as a woven gauze-double leno with twill weave having velour loops only on the outside surface. After weaving is completed the new tubular grafts are processed for shrinking, which controls the density of the fabric and thus the porosity discussed above as regards tissue ingrowth and control of hemorrhaging. The final diameter of these grafts is between about 2 to 34 mm. Porosity will be between 25 and 100 ml/min/cm$^2$/120 mm Hg. Lastly, the circumferential ribs or corrugations are formed under heated conditions and set.

While the invention has been described in terms of certain preferred embodiments, modifications obvious to one with ordinary skill in the art may be made without departing from the teachings of the present invention.

Various features of the invention are set forth in the following claims.

What is claimed:

1. A vascular graft prosthesis comprising a tube formed of woven fabric and attachable into a the vascular system for conveyance of blood therethrough, the fabric being a weave having a plurality of warp threads running in the axial direction of the tube and a plurality of weft threads running in a transverse direction to said axial direction, said warp threads being in sets of lenos and sets of plain and twill threads, the sets being in a repeating sequence where eact set of lenos is followed by a set of plain and twill threads, and where each leno comprises a pair of warp threads crossed one over the other between weft threads, each set of lenos comprises at least two adjacent lenos, and each set of plain and twill threads comprises at least four alternating plain and twill threads, the twill threads forming velour loops only on one surface of said fabric which fabric as a vascular graft has a resulting porosity that permits endothelization and substantially prevents hemorrhaging.

2. A woven fabric adapted for use in a vascular prosthesis for implantation into a living body, the fabric being a weave having a plurality of warp threads running in the axial direction of the tube and a plurality of weft threads running in a transverse direction to said axial direction, said warp threads being in sets of lenos and sets of plain and twill threads, the sets being in a repeating sequence where each set of lenos is followed by a set of plain and twill threads, and where each leno comprises a pair of warp threads crossed one over the other between weft threads, each set of lenos comprises at least two adjacent lenos, and each set of plain and twill threads comprises at least four alternating plain and twill threads, the twill threads forming velour loops only on one surface of said fabric which fabric as a vascular graft has a resulting porosity that permits endothelization and substantially prevents hemorrhaging.

3. A vascular graft prosthesis comprising a tube formed of woven fabric and attachable a the vascular system for conveyance of blood therethrough, the fabric being a weave having a plurality of warp threads running in the axial direction of the tube and a plurality of weft threads running in a transverse direction to said axial direction, said warp threads being in sets of lenos and sets of plain and parallel twill threads, the sets being in a repeating sequence where each set of lenos is followed by a set of plain and parallel twill threads, and where each leno comprises a pair of warp threads crossed one over the other between weft threads, each set of lenos comprises at least two adjacent lenos, and each set of plain and parallel twill threads comprises at least four alternating plain and parallel twill threads, the parallel twill threads forming velour loops only on one surface of said fabric which fabric as a vascular graft has a resulting porosity that permits endothelization and substantially prevents hemorrhaging.

4. A woven fabric adapted for use in a vascular prosthesis for implantation into a living body, the fabric being a weave having a plurality of warp threads running in the axial direction of the tube and a plurality of weft threads running in a transverse direction to said axial direction, said warp threads being in sets of lenos and sets of plain and parallel twill threads, the sets being in a repeating sequence where each set of lenos is followed by a set of plain and parallel twill threads, and where each leno comprises a pair of warp threads crossed one over the other between weft threads, each set of lenos comprises at least two adjacent lenos, and each set of plain and parallel twill threads comprises at least four alternating plain and parallel twill threads, the parallel twill threads forming velour loops only on one surface of said fabric which fabric as a vascular graft has a resulting porosity that permits endothelization and substantially prevents hemorrhaging.

5. A graft according to claim 1 wherein each of said filaments comprises polyethylene terephthalate weighing less than 1.0 gram per 9,000 meters.

6. A graft according to claim 1 wherein each of said filaments comprises polyethylene terephthalate weighing from 0.4 grams to 1.0 gram per 9,000 meters.

7. A graft according to claim 1 wherein said threads comprise texturized 64 denier/144 filament polyester.

8. A graft according to claim 1 wherein said weave pattern when initially woven comprises warp threads in the range of 140 to 170 threads per inch and weft threads in the range of 60 to 80 threads per inch.

9. A graft according to claim 1 wherein all said warp and weft threads except the velour threads are not pre-shrunk before being woven.

10. A graft according to claim 4 wherein said weave after shrinkage comprises warp threads in the range of 140 to 170 threads per inch, and weft threads in the range of 70 to 80 threads per inch.

11. A graft according to claim 1 wherein all said threads are texturized to have about 1 1/2 turns per inch of length.

12. A graft according to claim 1 wherein each plain/twill set comprises 3/1 twill threads alternating with 1/1 plain threads.

13. A graft according to claim 1 wherein each plain/twill set comprises between 4 and 8 warp threads woven in alternating 1/1 plain and 3/1 weave.

14. A graft according to claim 1 wherein for each of the plain/twill sets one of the plain strands is advanced longitudinally by one weft strand relative to the next plain strand.

15. A graft according to claim 1 wherein said tube comprises a first part of first diameter, and one end of said first part is bifurcated and extends as two tubes of diameter smaller than said first diameter.

16. A graft according to claim 1 wherein said threads comprise texturized 75 denier/72 filament polyester yarn.

17. A fabric according to claim 2, wherein said warp threads and said weft threads comprise texturized 64 denier/144 filament polyester.

18. A fabric according to claim 2, wherein said warp threads and said weft threads comprise texturized 75 denier/72 filament polyester.

19. A fabric according to claim 2, wherein each plain/twill set comprises between 4 and 8 warp threads in alternating 1/1 plain and 3/1 twill weave.

20. A graft according to claim 1 wherein said fabric has a flat interior surface and a velour loop exterior surface to receive tissue ingrowth.

* * * * *

UNITED STATES PATENT AND TRADEMARK OFFICE
CERTIFICATE OF CORRECTION

PATENT NO. : 4,816,028

DATED : March 28, 1989

INVENTOR(S) : Indu Kapadia, et al.

It is certified that error appears in the above-identified patent and that said Letters Patent is hereby corrected as shown below:

Column 2, line 19, change "50,000" to --250,000--;

Column 4, line 20 after "around" insert --the tube--;

line 22, after "threads" omit --the tube.

Column 5, change "11/2" to --1 1/2--.

Signed and Sealed this

Sixteenth Day of January, 1990

Attest:

JEFFREY M. SAMUELS

Attesting Officer     Acting Commissioner of Patents and Trademarks